United States Patent
Kopperschmidt et al.

(10) Patent No.: US 8,617,093 B2
(45) Date of Patent: Dec. 31, 2013

(54) METHOD AND DEVICE FOR MONITORING A FLUID SYSTEM OF AN EXTRACORPOREAL BLOOD TREATMENT DEVICE

(75) Inventors: Pascal Kopperschmidt, Dittelbrunn (DE); Thomas Nuernberger, Burkardroth (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 203 days.

(21) Appl. No.: 13/376,650

(22) PCT Filed: Jun. 1, 2010

(86) PCT No.: PCT/EP2010/003329
§ 371 (c)(1),
(2), (4) Date: Dec. 7, 2011

(87) PCT Pub. No.: WO2010/142394
PCT Pub. Date: Dec. 16, 2010

(65) Prior Publication Data
US 2012/0083726 A1    Apr. 5, 2012

(30) Foreign Application Priority Data
Jun. 9, 2009    (DE) .......................... 10 2009 024 864

(51) Int. Cl.
*A61M 37/00*    (2006.01)
(52) U.S. Cl.
USPC ........................................... 604/6.1
(58) Field of Classification Search
USPC ............. 604/4.04–6.16, 29–31, 90, 118, 119, 604/122, 149; 210/646, 739, 741
See application file for complete search history.

(56) References Cited

U.S. PATENT DOCUMENTS

| | | | |
|---|---|---|---|
| 7,069,788 B2 | 7/2006 | Teugels | |
| 7,516,665 B2 | 4/2009 | Teugels | |
| 8,192,388 B2 * | 6/2012 | Hogard | 604/6.11 |
| 2005/0132826 A1 | 6/2005 | Teugels | |
| 2007/0014689 A1 | 1/2007 | Teugels | |
| 2009/0071911 A1 | 3/2009 | Folden et al. | |

FOREIGN PATENT DOCUMENTS

| | | |
|---|---|---|
| DE | 10 033 192 A1 | 1/2002 |
| DE | 10 2005 001 779 A1 | 9/2006 |
| EP | 0 330 761 A1 | 9/1989 |
| EP | 1 547 630 A1 | 6/2005 |

OTHER PUBLICATIONS

PCT International Search Report from PCT/EP2010/003329, mailed on Sep. 29, 2010.
International Preliminary Report on Patentability from PCT/EP2010/003329, mailed on Dec. 12, 2011.

* cited by examiner

*Primary Examiner* — Philip R Wiest
(74) *Attorney, Agent, or Firm* — Kenyon and Kenyon LLP

(57) ABSTRACT

The present invention relates to a method and a device for monitoring a fluid system of an extracorporeal blood treatment device. In the method according to the present invention and the device according to the present invention, the pressure in a ventilation line branching off the venous drip chamber in the venous blood line is measured, a hydrophobic filter being disposed in the ventilation line. A fault in the fluid system is determined in the absence of pressure variations in the segment of the ventilation line remote from the venous drip chamber. The pressure variations in the ventilation line can be generated downstream of the hydrophobic filter by alternately ventilating the ventilation line that is closed downstream of the hydrophobic filter during blood treatment.

15 Claims, 2 Drawing Sheets

METHOD AND DEVICE FOR MONITORING A FLUID SYSTEM OF AN EXTRACORPOREAL BLOOD TREATMENT DEVICE

CROSS REFERENCE TO RELATED APPLICATIONS

This is a 371 national phase application of PCT/EP2010/003329 filed Jun. 1, 2010, claiming priority to German Patent Application No. 10 2009 024 864.1 filed Jun. 9, 2009.

FIELD OF INVENTION

The present invention relates to a method for monitoring a fluid system of an extracorporeal blood treatment apparatus which comprises an extracorporeal blood circuit having an arterial blood line, leading to a first chamber of a dialyser or filter subdivided into the first chamber and a second chamber by a semipermeable membrane, and a venous blood line leading away from the first chamber of the dialyser or filter. Moreover, the present invention relates to an apparatus for monitoring a fluid system of an extracorporeal blood treatment apparatus and to an extracorporeal blood treatment apparatus with an apparatus for monitoring the fluid system.

BACKGROUND OF THE INVENTION

The extracorporeal blood circuit of known blood treatment apparatuses comprises a device for separating air, generally also referred to as an air separator, in addition to the arterial and venous blood line, and the blood chamber of the dialyser or filter. The air separator has a chamber through which blood flows. In the process, the chamber of the air separator is not completely filled with blood. A monitoring device is used to monitor whether the chamber is filled with blood. Known drip chambers, arranged in the venous blood line downstream of the dialyser or filter, are used as air separators.

In known blood treatment apparatuses, a line generally branches off from the venous drip chamber, by means of which line the fluid system of the blood treatment apparatus can be ventilated during the filling of the extracorporeal blood circuit. The ventilation line is closed during the blood treatment.

In principle, there is a risk of the blood level in the venous drip chamber rising to the extent that blood enters the ventilation line during the extracorporeal blood treatment. As a safety measure, at least one hydrophobic filter, which is impermeable to fluid but permeable to air as long as the filter is not wetted by fluid, is arranged in the ventilation line.

Thus, the hydrophobic filter can effectively retain the blood, even if blood should enter the ventilation line. However, it is disadvantageous that the filter has to be cleaned or replaced after it has been wetted by blood, which results in an interruption of the blood treatment and constitutes a considerable amount of effort.

Before or after the dialysis, the extracorporeal blood circuit can be rinsed, for example using a sodium chloride solution or substitute (permeate of the dialysis fluid). In this case, there is also a risk of substitute fluid from the venous drip chamber reaching the hydrophobic filter via the ventilation line.

It may be possible to intervene in the machine control in the case of a fault. By way of example, the blood pump could be halted and the venous tube clamp could be closed. If no intervention is undertaken in the machine control in the case of a fault, there is, in principle, the risk of the membrane of the hydrophobic filter being pierced. It is possible that only one hydrophobic filter is present and it can be located in the ventilation line outside of, or, further down the line, also within, the machine. The risk of fluid entering the ventilation line can be reduced if two or more hydrophobic filters, connected in series, are arranged in the ventilation line. While the first hydrophobic filter, which can be arranged outside of the housing of the blood treatment apparatus, can still be cleaned or replaced in a relatively simple fashion, cleaning or replacing the second hydrophobic filter however requires the housing of the blood treatment apparatus to be opened.

EP 0 330 761 A1 describes a method for monitoring the fluid system of an extracorporeal blood treatment apparatus in which the pressure in the ventilation line in which a hydrophobic filter is arranged and which branches off from the venous drip chamber is monitored. The pressure is monitored in the section of the ventilation line remote from the drip chamber. In the process, periodic pressure variations are monitored which are generated by the blood pump and propagate across the tube system via the hydrophobic filter. Should blood enter the ventilation line, the membrane of the hydrophobic filter is wetted by fluid. As a result, the membrane of the hydrophobic filter becomes impermeable to air and so the periodic pressure variations can no longer spread out across the membrane of the hydrophobic filter. Therefore, the absence of periodic pressure variations is an indicator for a fault.

Should the natural pressure variations caused by the design of the peristaltic blood pump not be sufficient, EP 0 330 761 A1 proposes to amplify the natural pressure variations and generate artificial feed rate variations of the blood pump, for example by changing the pump rotational speed.

SUMMARY OF THE INVENTION

The present invention is based on the object of specifying a method which permits reliable monitoring of the fluid system of an extracorporeal blood treatment apparatus in order to be able to at least reliably prevent a piercing of the membrane of the hydrophobic filter in the case of a fault, but also to be able to already rule out the wetting of the membrane of the hydrophobic filter, or to at least detect this at an early stage. It is a further object of the present invention to provide an apparatus for reliably monitoring the fluid system of an extracorporeal blood treatment apparatus, as well as an extracorporeal blood treatment apparatus with an apparatus for monitoring the fluid system.

In the method according to the present invention and the apparatus according to the present invention, the pressure is monitored in the section of the ventilation line remote from the venous drip chamber, i.e. in that section which, when viewed from the venous drip chamber, lies behind the first hydrophobic filter, i.e. the pressure is measured downstream of the at least one hydrophobic filter, with a fault being inferred if pressure variations are absent. The ventilation line can be an individual tap line. However, it is also possible for the ventilation line to have a number of branching line sections. All that is important is that the ventilation line is a closed system.

In order to generate the periodic pressure variations, a first embodiment of the method according to the present invention and the apparatus according to the present invention provides for the venous locking organ, in general a venous tube clamp, arranged in the venous blood line, to be alternately at least partly closed and opened so that the fluid level in the venous drip chamber alternately rises and falls, as a result of which pressure variations are generated which propagate as far as the ventilation line.

An alternative, particularly preferred embodiment of the method according to the present invention and the apparatus according to the present invention provides for the pressure variations in the section of the ventilation line remote from the venous drip chamber, i.e. downstream of the at least one hydrophobic filter, to be generated by the ventilation line, which is closed off during the blood treatment and arranged downstream of the at least one hydrophobic filter, being alternately ventilated downstream of the at least one hydrophobic filter, i.e. in the section of the ventilation line remote from the venous drip chamber, so that the pressure is modulated in the ventilation line. That is to say, in this alternative embodiment, it is not pressure variations which are generated in the extracorporeal blood circuit, in particular by the blood pump, and propagate across the membrane of the at least one hydrophobic filter that are monitored, but rather pressure variations are monitored which are generated by the ventilation in the ventilation line itself.

In known blood treatment apparatuses, the ventilation line is in any case closed off by a ventilation valve which only has to alternately be opened and closed in order to generate the periodic pressure variations. It is for this reason that only relatively little technical effort is required for implementing the pressure monitoring.

In order to be able to build up the pressure in the ventilation line, the blood pump arranged in the extracorporeal blood circuit has to be operational and the venous locking organ has to at least in part be closed. If the locking organ is closed in part, the blood treatment does not have to be interrupted. However, complete closure of the venous locking organ assumes an interruption of the blood treatment for the duration of the monitoring. However, the pressure in the ventilation line can in principle also be built up using other means, e.g. by a compressor or the like.

Monitoring the fluid system is based on the fact that in the case of a fault it is no longer possible to detect the pressure variations. To this end, different criteria can be set. All that is important is that the occurrence or lack of pressure variations is monitored. Such faults can be due not only to hydrophobic membranes (TDPs) being wetted by fluid and hence being impermeable to air, but also, for example, due to hydrophobic membranes sticking together due to production faults and therefore being impermeable to air, or due to hydrophobic membranes which are not connected.

In a preferred embodiment, a check is performed as to whether a pressure rise can be detected. By way of example, a pressure rise can be detected by the pressure rising above a predetermined limit value. However, it is also possible to determine the gradient of the measured pressure signal, a pressure rise being inferred if the gradient of the measured signal exceeds a predetermined limit value. By correspondingly setting the limit value, it is possible not only to rule out the wetting of the membrane of the hydrophobic filter but also to recognize this at an early stage.

If the variations of the pressure signal are absent during a fault, an acoustic and/or optical alarm is preferably emitted. Preferably, in the case of a fault, intervention is also undertaken in the control of the extracorporeal blood treatment apparatus. The blood pump is preferably halted so that blood cannot continue to flow into the ventilation line.

BRIEF DESCRIPTION OF THE DRAWINGS

In the following text, exemplary embodiments of the present invention are explained in more detail with reference to the drawings, in which.

DETAILED DESCRIPTION OF THE DRAWINGS

Figure 1:
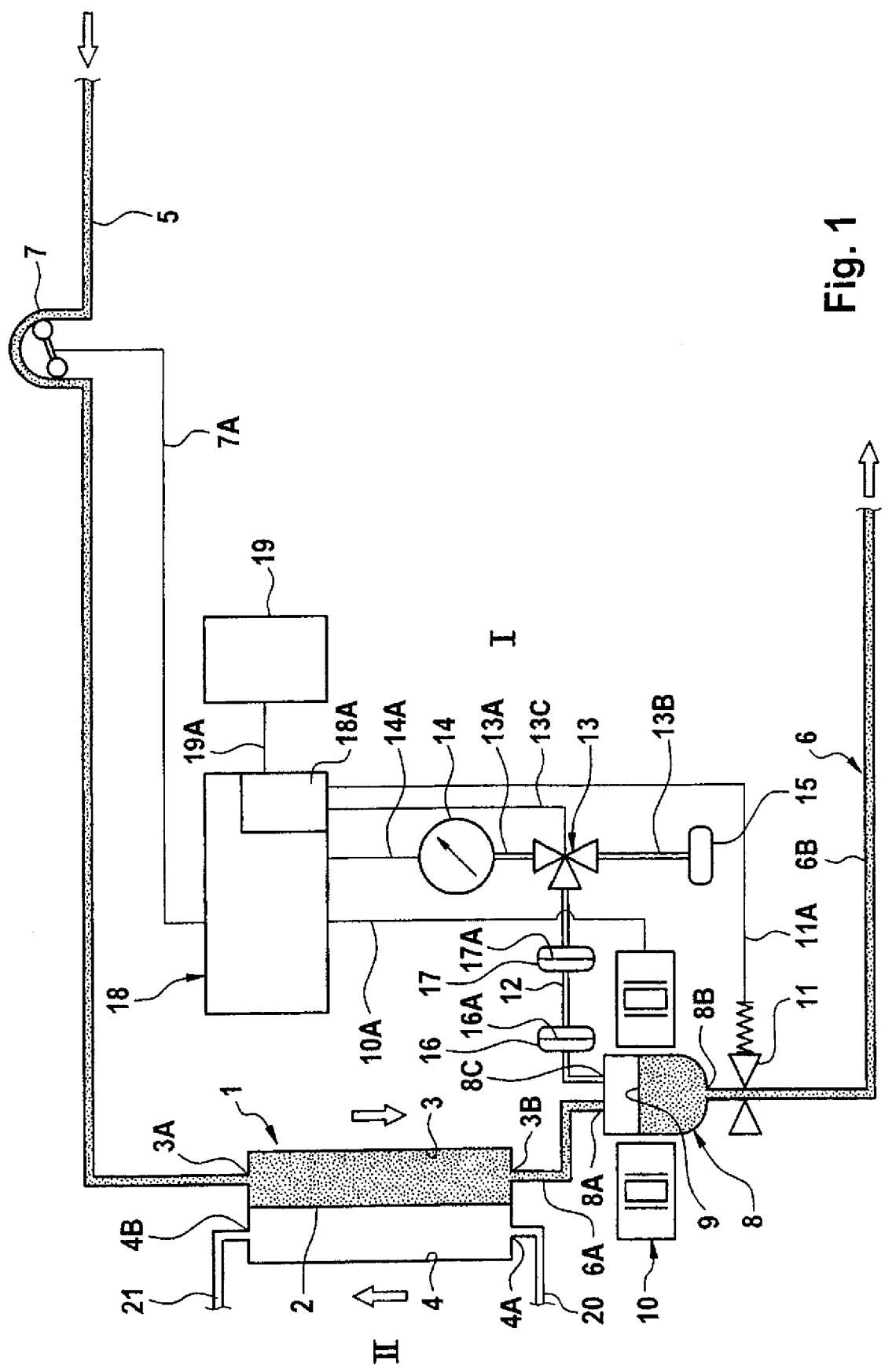
FIG. 1 shows, in a very simplified schematic illustration, a first exemplary embodiment of an apparatus for extracorporeal blood treatment with an apparatus for monitoring the fluid system.

FIG. 1 shows the essential components of a first exemplary embodiment of an extracorporeal blood treatment apparatus with an apparatus for monitoring the fluid system. The extracorporeal blood treatment apparatus can, for example, be an apparatus for haemodialysis (HD) or haemofiltration (HF), or an apparatus permitting both haemodialysis and haemofiltration (a haemo(dia)filtration apparatus). It is for this reason that the blood treatment apparatus can have a dialyser or filter.

In the following text, a blood treatment apparatus with the apparatus for monitoring the fluid system will be described. In practice, this will be the case because the apparatus for monitoring the fluid system makes use of individual components which in any case are present in the blood treatment apparatus. However, it is also possible for the monitoring apparatus to form an individual unit.

The extracorporeal blood treatment apparatus, in particular haemo(dia)filtration apparatus, comprises a dialyser 1 or filter which is subdivided into a first chamber 3 and a second chamber 4 by a semipermeable membrane 2. An arterial blood line 5 runs from the patient to the inlet 3A of the first chamber 3 of the dialyser 1. A venous blood line 6 leads from the outlet 3B of the blood chamber 3 to the patient. A peristaltic blood pump 7 is arranged in the arterial blood line 5 for the purpose of conveying blood. A venous drip chamber 8 is arranged in the venous blood line 6, downstream of the blood chamber 3, and it prevents air from reaching the patient. Blood flows through the venous drip chamber 8 during the extracorporeal treatment of blood. Before or after the treatment, it is possible for a substitute fluid, in particular a sodium chloride solution, to flow through the drip chamber.

The blood flows from the blood chamber 3, via a first line section 6A of the venous blood line 6, to an inlet 8A of the venous drip chamber 8 which is arranged on the cover of said drip chamber 8. The blood flows to the patient, via a line section 6B of the venous blood line 6, from an outlet 8B at the base of the venous drip chamber 8. A fluid level 9 forms in the drip chamber. In the present exemplary embodiment, a device 10 monitors the height of the fluid level 9, in particular the blood level. However, it is also possible for the device to only be used to monitor whether the drip chamber is filled with blood in order to rule out the drip chamber running empty, as is known from the prior art. A venous locking organ 11, in particular a tube clamp which can be actuated electromagnetically and can be closed in the case of a fault so that no more blood reaches the patient, is arranged in the line section 6B of the venous blood line 6, downstream of the venous drip chamber 8. A ventilation line 12 branches off from a second outlet 8C on the cover of the drip chamber 8 and it leads to a three-way valve 13 which can be actuated electromagnetically.

A measuring unit 14 for measuring the pressure in the ventilation line 12 is connected to the one branch 13A of the three-way valve 13, while a pressure reducer 15 is connected to the other branch 13B.

Two hydrophobic filters 16, 17 are arranged in the ventilation line 12 between the venous drip chamber 8 and the three-way valve 13, of which the first hydrophobic filter 16 is arranged outside of the housing (not illustrated) of the blood treatment apparatus, and the second hydrophobic filter 17 is arranged within the housing of the blood treatment apparatus so that it is still relatively easy to access the first hydrophobic filter 16, but it is relatively hard to access the second hydrophobic filter 17. Both hydrophobic filters 16, 17 have a hydrophobic membrane 16A, 17A.

The extracorporeal blood treatment apparatus comprises a central control and computational unit 18 which is used to control the individual components of the blood treatment apparatus according to the specifications of the user. In the present exemplary embodiment, the central control and computational unit 18 of the blood treatment apparatus also comprises the control unit, or the control and computational unit, of the apparatus for monitoring the fluid system. However, the monitoring apparatus can also comprise a separate control unit or control and computational unit. Optionally, the central control and computational unit 18 is connected to the blood pump 7 via a control line 7A, to the venous tube clamp 11 via a control line 11A, and to the three-way valve 13 via a control line 13C. The control and computational unit 18 is connected to the monitoring device 10 for the blood level via a data line 10A, and to the measuring unit 14 for measuring the pressure in the ventilation line 12 via a data line 14A.

Moreover, provision is made for an alarm unit 19 which emits an acoustic and/or optical alarm. The alarm unit 19 is connected to the control and computational unit 18 via a data line 19A.

In addition to the extracorporeal blood circuit I, the extracorporeal blood treatment apparatus comprises a dialysis fluid circuit II, which is only illustrated in outlines. It has a dialysis fluid supply line 20 which leads to the inlet 4A of the second chamber 4 of the dialyser 1, and a dialysis fluid outflow line 21, which leads away from the outlet 4B of the dialysis fluid chamber.

In order to fill the extracorporeal blood circuit I, the central control and computational unit 18 actuates the three-way valve 13 such that a connection is made to the pressure reducer 15 for the purpose of ventilating the system. It follows that air can escape from the venous drip chamber 8 via the ventilation line 12 and the pressure reducer 15. By contrast, during the blood treatment, the control and computational unit 18 actuates the three-way valve 13 such that a connection is made to the pressure measuring unit 14. Hence, the ventilation line is closed off at the end.

If the venous tube clamp 11 is closed and the blood pump 7 is operated, the blood level 9 increases in the venous drip chamber 8, as a result of which there is a pressure increase which can be detected by the measuring unit 14, in the chamber 8 and the ventilation line 12, which is closed off at the end and branches off from said chamber.

First of all, the monitoring device 10 for the fluid level will be activated when a predetermined upper blood level is exceeded in the venous drip chamber 8, which monitoring device is connected to the control and computational unit 18 via the data line 10A. The monitoring device 10 then generates a control signal which is received by the control and computational unit 18.

The control and computational unit 18 comprises a unit 18A which generates a control signal for intervening in the machine control when it receives the control signal of the monitoring device 10. Thereupon the blood pump 7 is halted so that the blood level 9 no longer continues to rise.

In the present exemplary embodiment, the apparatus according to the present invention for monitoring the fluid system constitutes a redundant system which is only used if the monitoring device 10 for the fluid level fails. The apparatus according to the present invention for monitoring the fluid system can also be used as a redundant system if the monitoring device only monitors the presence of blood in the venous drip chamber. However, the apparatus according to the present invention can also operate completely independently of the monitoring device. Even though blood is discussed in the present case, the apparatus according to the present invention can also prevent the wetting or destruction of the membrane of a hydrophobic filter by a substitute fluid before or after the treatment.

A first embodiment of the monitoring apparatus according to the present invention provides for the central control and computational unit 18 to at least partly close the venous locking organ 11 for a predetermined first interval of time in order to then completely reopen the venous tube clamp 11 for a predetermined second interval of time which can be identical to the first interval of time. The tube clamp is alternately opened and closed. Since known tube clamps used in practice only permit a completely opened and closed state for safety reasons in particular, the blood flow will have to be completely interrupted in practice. However, in practice, it is also possible for the venous blood line 6 to be only partly closed.

Alternately opening and closing the venous tube clamp 11 generates periodic pressure variations in the fluid system of the blood treatment apparatus comprising the ventilation line 12; said periodic pressure variations are measured by the pressure measuring unit 14. The control and computational unit 18 evaluates the measured pressure signal in order to be able to detect a fault. Here, a fault is inferred if the pressure variations are absent. The absence of pressure variations is explained by the fact that the hydrophobic membrane 16A of the first filter 16 of the two hydrophobic filters 16, 17 arranged in series is wetted by blood in the case of a fault. As a result, the hydrophobic membrane 16A is no longer permeable to air either. It follows that the pressure variations generated in the extracorporeal blood circuit I can no longer be detected by the pressure measuring unit 14 in the ventilation line 12 downstream of the hydrophobic filter 16.

A particularly preferred alternative embodiment provides for the periodic pressure variations in the fluid system not to be generated by the venous tube clamp 11, but rather by the ventilation line 12 being ventilated for a predetermined interval of time when the blood pump 7 is in operation and the venous locking organ 11 is at least partly closed. When the blood pump 7 is operational and the venous tube clamp 11 is closed, the blood level 9 in the venous drip chamber 8 continuously increases, as a result of which the pressure in the ventilation line 12, which is closed off at the end, increases in turn. Therefore, ventilating the ventilation line 12 leads to a pressure drop in the ventilation line 12 and the venous drip chamber 8, and a fall in the blood level 9 in the drip chamber 8.

The control and computational unit 18 actuates the venous locking organ 11 such that the locking organ 11 is closed for a predetermined interval of time. During this predetermined interval of time Δt, the control and computational unit 18 then actuates the three-way valve 13 such that the connection to the pressure reducer 15 is alternately opened and closed so that the ventilation line is ventilated from time to time. The alternating opening and closing of the ventilation valve 13 is preferably synchronized with the rotation of the peristaltic blood pump 7 which is used to compress the volume of air.

Figure 2:
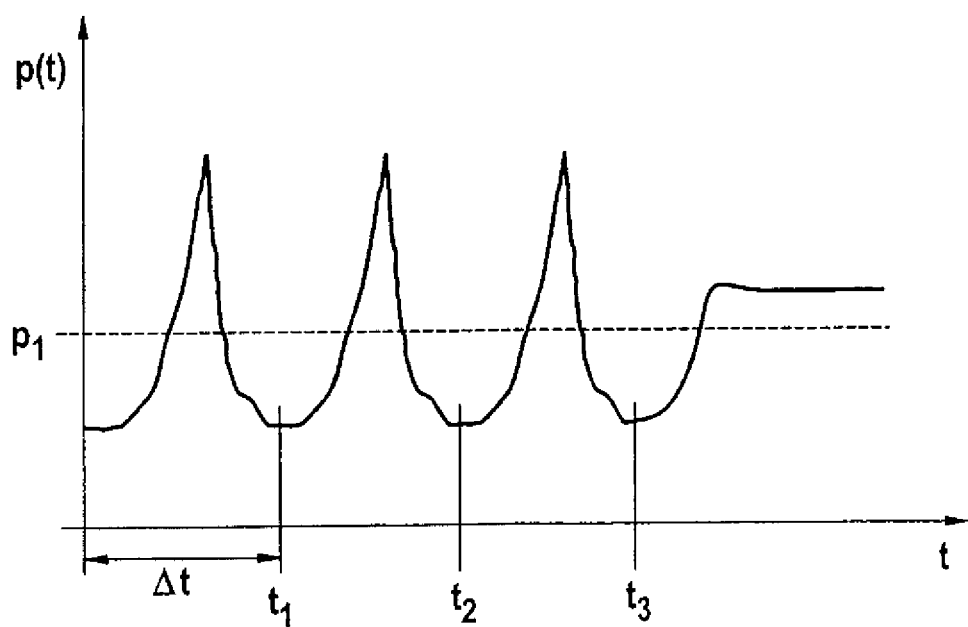
FIG. 2 shows the profile of the measured pressure signal for monitoring the fluid system.

FIG. 2 shows the pressure signal p(t) measured by the pressure measuring unit 14 as a function of time t. It can be seen that the pressure firstly increases when the blood pump 7 is operational and the venous locking organ 11 is closed, before falling back to its original value at the time $t_1$ after the interval of time Δt has passed. This process is then repeated periodically so that an oscillating pressure signal p(t), which is measured by the measuring unit 14, is generated.

Should the membrane 16A of the first filter 16 of the two hydrophobic filters 16, 17 connected in series be wetted by blood such that the filter now also becomes impermeable to air, then the pressure in the ventilation line 12 can no longer be built up to the original value. It follows that the lack of oscillation of the pressure signal p(t) can be used to reliably infer a fault.

The central control and computational unit 18 monitors the pressure signal p(t) during the pressure measurement, with a check being performed as to whether a predetermined rise or fall in pressure can be detected after every ventilation, i.e. after closing the ventilation valve 13. By way of example, the control and computational unit 18 checks whether the pressure rises above a predetermined limit value $p_1$. In the exemplary embodiment, this is the case after the third period. The evaluation permits detection of the wetting of the hydrophobic membrane within such a short period of time that a volume of only a few milliliters of blood is pumped before the control and computational unit 18 intervenes in the machine control by stopping the blood pump 7. Instead of monitoring a predetermined limit value $p_1$ for the pressure signal p(t), it is also possible for the control and computational unit 18 to calculate and monitor the gradient of the pressure signal p(t). Intervention is undertaken in the machine control when the gradient of the pressure signal p(t) undershoots a predetermined limit value after the ventilation valve 13 is closed, i.e. when a significant increase of the pressure signal is no longer recorded.

The gradient profile of the pressure signal p(t) can be used to infer the residual volume amount in the fluid system, in particular when the ventilation valve is closed. The Boyle-Mariotte law follows from the general gas equation in isothermal conditions; it states that the decrease in volume is the reciprocal of the increase in pressure:

$$\Delta V \propto \frac{1}{\Delta p}$$

The above equation allows the estimation of the compressed residual volume V compared to $V_0$, using the absolute pressure p compared to $p_0$. In this case, the boundary conditions are given by $V_0 \cdot p_0 = c$. The constant c describes the compliance of the pneumatic system.

$$V = V_0 + \frac{\partial V}{\partial p}(p_0 + p) = V_0 - \frac{c}{p_0 + p}$$

Since both the tube lines and the drip chamber are subject to production-dependent tolerances, changes can be expected in the air volume enclosed in the corresponding tube lines and in the drip chamber. In addition, there are fluctuations in the surrounding temperature. In practice, this can be problematic when evaluating the measurement values.

The ideal gas law pV=nRT shows that, in the case of an identical blood level, the detected pressure can change as a result of variations of the enclosed volume of air only. Therefore, provision is made for a calibration of the measurement apparatus according to the present invention, which can be effected by the operating staff starting an appropriate calibration program. To this end, the tube set with the arterial and venous blood lines 5, 6 is firstly filled with the venous tube clamp 11 being closed. With the blood pump 7 in slow operation, the blood level 9 is observed in the drip chamber 8. Once the blood level reaches a critical upper limit value, the operator prescribes the upper limit value as the limit value at which the blood pump 7 is stopped and the tube clamp 11 is opened. This prescription can be effected by a corresponding interaction with the machine, for example by pressing a button. The temperature can be considered to be sufficiently constant for the duration of the treatment. However, it is also possible to acquire the temperature using temperature sensors and to also take temperature changes into account when evaluating the measured pressure signal.

In principle, it is possible to generate pressure variations in the venous drip chamber using a compressor, the fluid level not changing in the drip chamber due to the negligible compressibility of liquids. To this end, the compressor can be connected to the system via an additional ventilation line in which at least one additional hydrophobic filter is arranged. Using the compressor, the air in the system can then alternately be compressed or relaxed. A wetting of the membrane of the hydrophobic filter to be monitored would result in it not being possible to detect pressure changes anymore and so a fault can be inferred.

What is claimed is:

1. A method for monitoring a fluid system of an extracorporeal blood treatment apparatus, said extracorporeal blood treatment apparatus comprising: a dialyser or filter subdivided into a first chamber and a second chamber by a semipermeable membrane, an extracorporeal blood circuit having an arterial blood line leading to the first chamber and a venous blood line leading away from the first chamber, a venous drip chamber arranged in the venous blood line downstream of the first chamber, a venous locking organ arranged in the venous blood line downstream of the venous drip chamber, a ventilation line branching off from the venous drip chamber, and at least one hydrophobic filter arranged in said ventilation line that can be closed off by a ventilation valve arranged in a section of the ventilation line remote from the venous drip chamber, said method comprising the following steps:
    measuring a pressure in the ventilation line in the section of the ventilation line remote from the venous drip chamber;
    alternately at least partly opening and closing the venous locking organ, whereby the fluid level in the venous drip chamber alternately rises and falls, as a result of which the measured pressure signal is subject to pressure variations if there is no fault;
    evaluating the measured pressure signal; and
    detecting a fault if pressure variations of the measured pressure signal are absent.

2. The method according to claim 1, wherein the extracorporeal blood treatment apparatus further comprises a blood pump arranged in the extracorporeal blood circuit.

3. The method according to claim 2, further comprising:
    if a fault is detected, halting the blood pump.

4. The method according to claim 1, further comprising:
    performing a check to determine whether a predetermined pressure rise is detected.

5. The method according to claim 1, further comprising:
    performing a check to determine whether the pressure rises above a predetermined limit value.

6. The method according to claim 1, further comprising:
    generating an acoustic alarm, an optical alarm, or both if a fault is detected.

7. The method according to claim 1, further comprising:
    if a fault is detected, intervening in the control of the extracorporeal blood treatment apparatus.

8. An apparatus for monitoring a fluid system of an extracorporeal blood treatment apparatus, the extracorporeal blood treatment apparatus comprising: a dialyser or filter subdivided into a first chamber and a second chamber by a semipermeable membrane, an extracorporeal blood circuit having an arterial blood line leading to the first chamber and a venous blood line leading away from the first chamber, a venous drip chamber arranged in the venous blood line downstream of the first chamber, a venous locking organ arranged in the venous blood line downstream of the venous drip chamber, a blood pump arranged in the extracorporeal blood circuit, a ventilation line branching off from the venous drip chamber, and at least one hydrophobic filter arranged in said ventilation line that can be closed off by a ventilation valve arranged in a section of the ventilation line remote from the venous drip chamber, wherein the apparatus for monitoring the fluid system comprises:

a measuring unit configured to measure the pressure in the ventilation line in the section of the ventilation line remote from the venous drip chamber; and a control and computational unit configured to evaluate the measured pressure signal and to determine there is a fault if pressure variations of the pressure signal are absent, wherein the control and computational unit is also configured to alternately at least partly open and close the venous locking organ whereby the fluid level in the venous drip chamber alternately rises and falls, as a result of which the measured pressure signal is subject to periodic pressure variations if there is no fault.

9. The apparatus according to claim 8, wherein the control and computational unit is also configured to alternately at least partly open and close the ventilation valve when the venous locking organ is at least partly closed.

10. The apparatus according to claim 8, wherein the control and computational unit is also configured such that a check is performed as to whether a predetermined pressure rise can be detected.

11. The apparatus according to claim 8, wherein the control and computational unit is also configured such that a check is performed as to whether the pressure rises above a predetermined limit value.

12. The apparatus according to claim 8, further comprising:

an alarm unit for generating an acoustic alarm, an optical alarm, or both, said alarm unit interacts with the control and computational unit such that the acoustic alarm, optical alarm, or both is generated if a fault is detected.

13. The apparatus according to claim 8, wherein the control and computational unit is also configured to generate a control signal for intervening in the control of the extracorporeal blood treatment apparatus if a fault is detected.

14. The apparatus according to claim 8, wherein the control and computational unit is also configured to halt the blood pump if a fault is detected.

15. An extracorporeal blood treatment apparatus comprising:

a dialyser or filter subdivided into a first chamber and a second chamber by a semipermeable membrane;

an extracorporeal blood circuit having an arterial blood line leading to a first chamber and a venous blood line leading away from the first chamber;

a venous drip chamber arranged in the venous blood line downstream of the first chamber;

a venous locking organ arranged in the venous blood line downstream of the venous drip chamber;

a blood pump arranged in the extracorporeal blood circuit;

a ventilation line branching off from the venous drip chamber;

at least one hydrophobic filter arranged in said ventilation line that can be closed off by a ventilation valve arranged in a section of the ventilation line remote from the venous drip chamber; and an apparatus for monitoring the fluid system of the extracorporeal blood treatment apparatus comprising:

a measuring unit configured to measure the pressure in the ventilation line in the section of the ventilation line remote from the venous drip chamber; and a control and computational unit configured to evaluate the measured pressure signal and to determine there is a fault if pressure variations of the pressure signal are absent, wherein the control and computational unit is also configured to alternately at least partly open and close the venous locking organ whereby the fluid level in the venous drip chamber alternately rises and falls, as a result of which the measured pressure signal is subject to periodic pressure variations if there is no fault.

* * * * *